US012268462B2

(12) United States Patent
Goldberg

(10) Patent No.: US 12,268,462 B2
(45) Date of Patent: Apr. 8, 2025

(54) SURGICAL DRAPE FOR ANESTHESIA ADMINISTRATION AREA

(71) Applicant: Grigory Goldberg, Belle Meade, NJ (US)

(72) Inventor: Grigory Goldberg, Belle Meade, NJ (US)

( * ) Notice: Subject to any disclaimer, the term of this patent is extended or adjusted under 35 U.S.C. 154(b) by 770 days.

(21) Appl. No.: 17/351,370

(22) Filed: Jun. 18, 2021

(65) Prior Publication Data

US 2021/0393360 A1    Dec. 23, 2021

Related U.S. Application Data

(60) Provisional application No. 63/041,520, filed on Jun. 19, 2020.

(51) Int. Cl.
*A61B 46/10* (2016.01)
*A61B 46/00* (2016.01)
*A61B 90/50* (2016.01)

(52) U.S. Cl.
CPC .............. *A61B 46/10* (2016.02); *A61B 46/40* (2016.02); *A61B 90/50* (2016.02)

(58) Field of Classification Search
CPC .... C07D 307/12; C07D 207/08; A61B 46/00; A61B 46/10; A61B 46/40; A61B 90/50; C07C 309/00; C07C 309/70
See application file for complete search history.

(56) References Cited

U.S. PATENT DOCUMENTS 10,213,267 B2 * 2/2019 King ...................... A61B 46/10

FOREIGN PATENT DOCUMENTS

AU           5928198 A  * 10/1998 ............... A61F 7/00

* cited by examiner

*Primary Examiner* — Lawrence D Ferguson
(74) *Attorney, Agent, or Firm* — Fox Rothschild LLP

(57) ABSTRACT

Surgical drapes for separating an anesthesia administration area from a surgical area are provided. The surgical drape includes a sterile front surface, a back surface, a surgical coupling mechanism configured to secure a lower portion of the surgical drape over a portion of a patient, and one or more upper coupling mechanisms configured to secure an upper portion of the surgical drape to one or more retention devices.

20 Claims, 4 Drawing Sheets

SURGICAL DRAPE FOR ANESTHESIA ADMINISTRATION AREA

CROSS-REFERENCE TO RELATED APPLICATION

The present application claims priority to U.S. Provisional Patent Application No. 63/041,520, filed Jun. 19, 2020, entitled "SURGICAL DRAPE FOR ANESTHESIA ADMINISTRATION AREA," which is incorporated herein by reference in its entirety.

TECHNICAL FIELD

The present disclosure relates to surgical drapes and, in particular, to dedicated surgical drapes configured to separate the anesthesia administration area from the remaining surgical area.

BACKGROUND

During medical procedures, surgical drapes are often used to establish and maintain a sterile environment around the area in which the medical procedure is being performed. The surgical drape performs this task by providing a sterile barrier that aids in the prevention of contaminants from entering the surgical site. This helps in preventing unwanted foreign objects from entering incisions during surgical procedures which may cause injury or infection, leading to further complications from the medical procedure.

Surgical drapes are often applied following the administration of anesthesia to the patient. However, the role of the anesthesiologist does not end here. During many medical procedures, the anesthesiologist must maintain access to a patient in order to properly administer anesthetics and monitor the patient's vital signs. Modern surgical drapes, however, are often cumbersome and not ideal for granting the anesthesiologist adequate access to the patient while simultaneously separating the surgical area from that required of the anesthesiologist.

For at least these reasons, properly separating the anesthesia administration area from the surgical area increases the anesthesiologist's access to the patient, enabling the anesthesiologist to better maintain the health and safety of the patient. A safe and effective surgical drape for separating the anesthesia administration area from the surgical area is thus needed.

SUMMARY

According to an aspect of the present disclosure, a surgical drape for separating an anesthesia administration area from a surgical area is provided. The surgical drape includes a sterile front surface, a back surface, a surgical coupling mechanism configured to secure a lower portion of the surgical drape over a portion of a patient, and one or more upper coupling mechanisms configured to secure an upper portion of the surgical drape to one or more retention devices.

According to various embodiments, the surgical drape further includes one or more window portions configured to enable a transparent view through the sterile front surface and the back surface.

According to various embodiments, the surgical drape further includes one or more window coverings configured to cover one or more portions of the one or more window portions.

According to various embodiments, the surgical drape further includes one or more pocket portions positioned on the sterile front surface or the back surface.

According to various embodiments, the surgical coupling mechanism includes one or more of the following: one or more adhesives; one or more hook and loop fasteners; or one or more snap fasteners.

According to various embodiments, the one or more adhesives includes one or more antimicrobial adhesives.

According to various embodiments, the surgical coupling mechanism forms a sterile barrier.

According to various embodiments, the sterile front surface includes one or more of the following: plastic; polyester; or cotton.

According to various embodiments, the sterile front surface forms a liquid barrier.

According to various embodiments, the one or more upper coupling mechanisms includes one or more of the following: one or more adhesives; one or more hook and loop fasteners; one or more buttons; one or more clips; or one or more snap fasteners.

According to various embodiments, the one or more retention devices includes one or more intravenous poles.

According to another aspect of the present disclosure, a surgical drape for separating an anesthesia administration area from a surgical area is provided. The surgical drape includes a center portion, and one or more side portions. The center portion and the one or more side portions each include a sterile front surface and a back surface. The surgical drape further includes a surgical coupling mechanism configured to secure a lower portion of the surgical drape over a portion of a patient, and one or more upper coupling mechanisms configured to secure an upper portion of the surgical drape to one or more retention devices.

According to various embodiments, the surgical drape further includes one or more window portions configured to enable a transparent view through the sterile front surface and the back surface.

According to various embodiments, the surgical drape further includes one or more window coverings configured to cover one or more portions of the one or more window portions.

According to various embodiments, the surgical drape further includes one or more pocket portions positioned on the sterile front surface or the back surface of the center portion or the one or more side portions.

According to various embodiments, the surgical coupling mechanism includes one or more of the following: one or more adhesives; one or more hook and loop fasteners; or one or more snap fasteners.

According to various embodiments, the one or more adhesives includes one or more antimicrobial adhesives.

According to various embodiments, the surgical coupling mechanism forms a sterile barrier.

According to various embodiments, the sterile front surface includes one or more of the following: plastic; polyester; or cotton.

According to various embodiments, the sterile front surface forms a liquid barrier.

According to various embodiments, the one or more upper coupling mechanisms includes one or more of the following: one or more adhesives; one or more hook and loop fasteners; one or more buttons; one or more clips; or one or more snap fasteners.

According to various embodiments, the one or more retention devices includes one or more intravenous poles.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1:
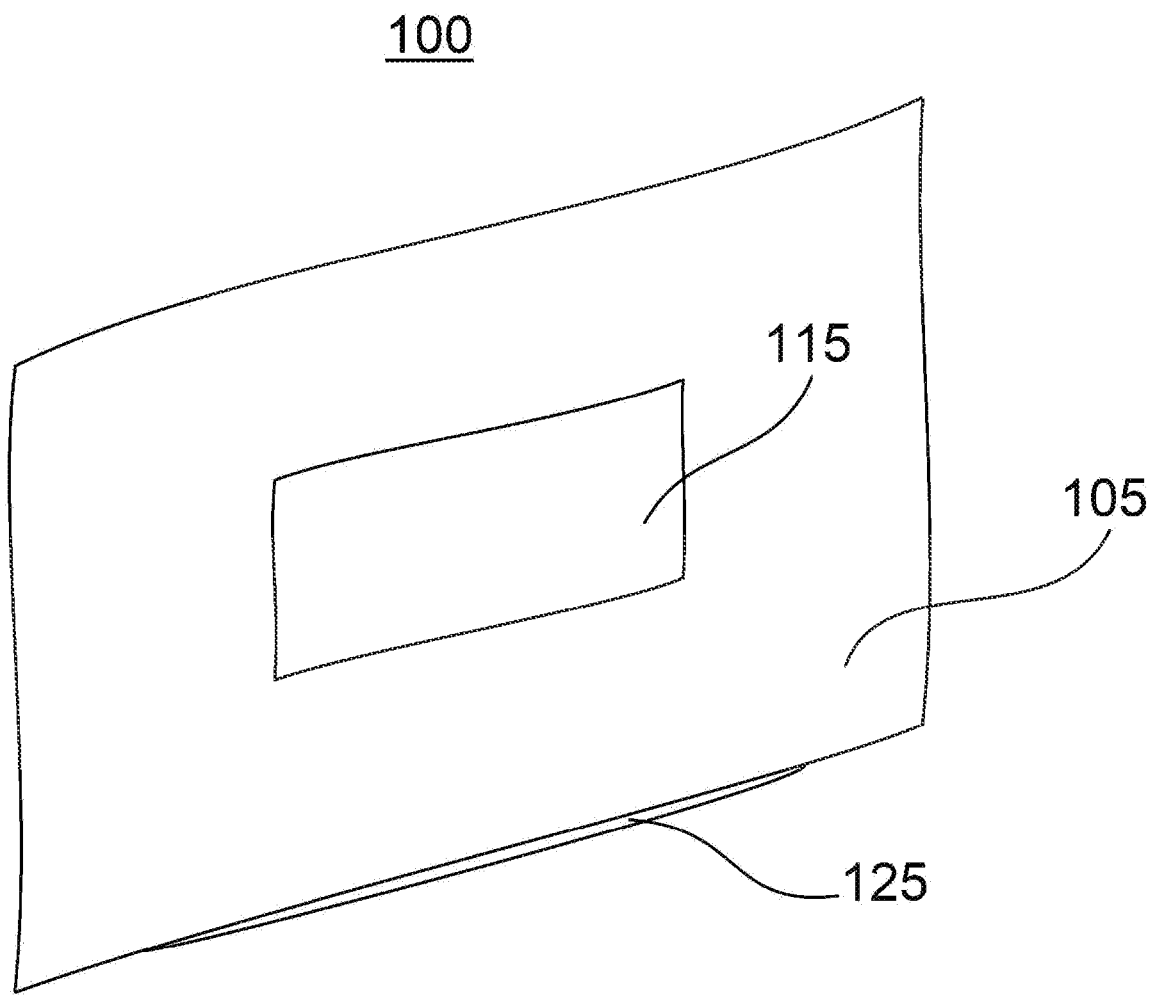
FIG. 1 is an example of a perspective view of a dedicated anesthesia surgical drape, in accordance with various embodiments of the present disclosure.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

As used in this document, the singular forms "a," "an," and "the" include plural references unless the context clearly dictates otherwise. Unless defined otherwise, all technical and scientific terms used herein have the same meanings as commonly understood by one of ordinary skill in the art. When used in this document, the term "comprising" (or "comprises") means "including (or includes), but not limited to." When used in this document, the term "exemplary" is intended to mean "by way of example" and is not intended to indicate that a particular exemplary item is preferred or required.

In this document, the term "approximately," when used in connection with a numeric value, is intended to include values that are close to, but not exactly, the number. For example, in some embodiments, the term "approximately" may include values that are within +/−10 percent of the value.

Other terms that are relevant to this disclosure are defined at the end of this Detailed Description section.

Figure 2:
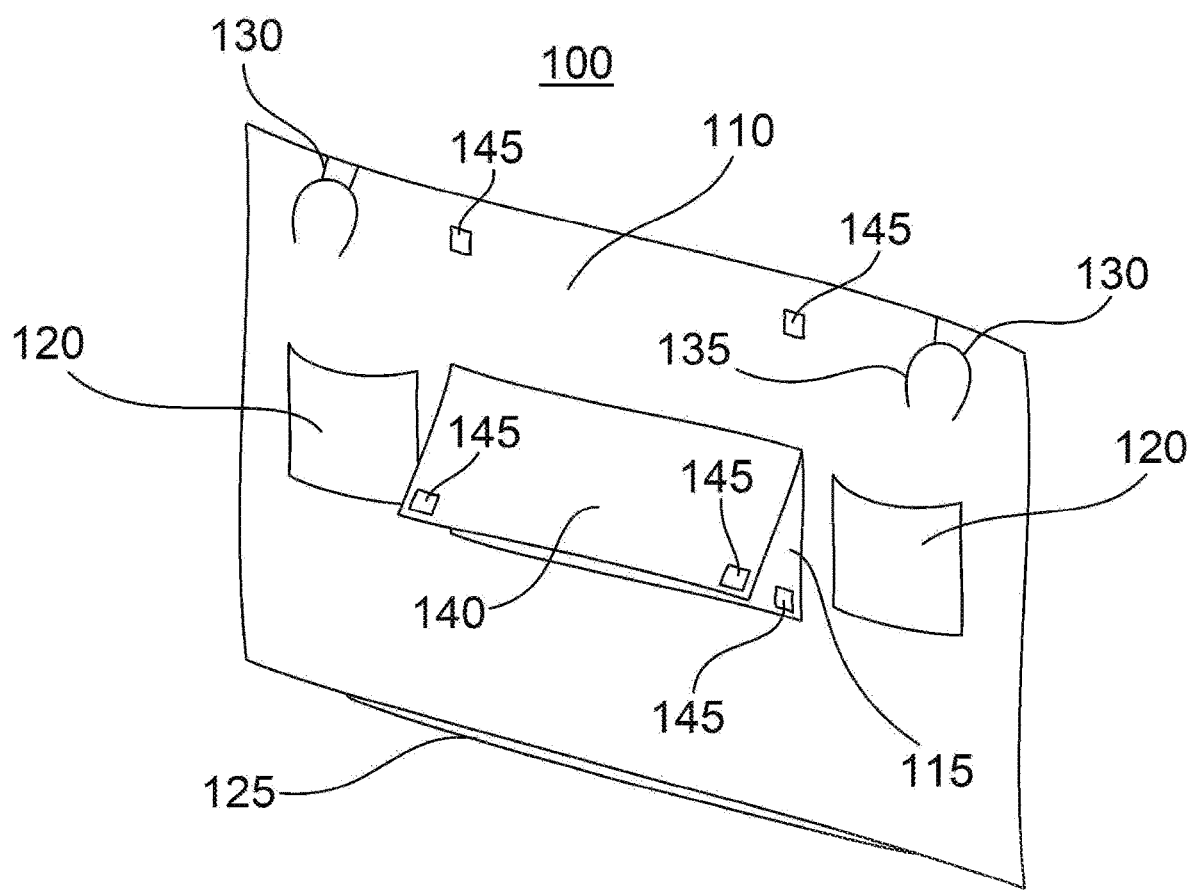
FIG. 2 is an example of a rear perspective view of a dedicated anesthesia surgical drape, in accordance with various embodiments of the present disclosure.

Referring now to FIGS. 1 and 2, a front perspective view (FIG. 1) and a rear perspective view (FIG. 2) of a dedicated anesthesia surgical drape 100, for separating the anesthesia administration area 150 which is dedicated for the administration of anesthesia for a patient during a surgical procedure from other surgical areas 155 during the procedure, are illustratively depicted in accordance with various embodiments of the present disclosure.

Figure 3:
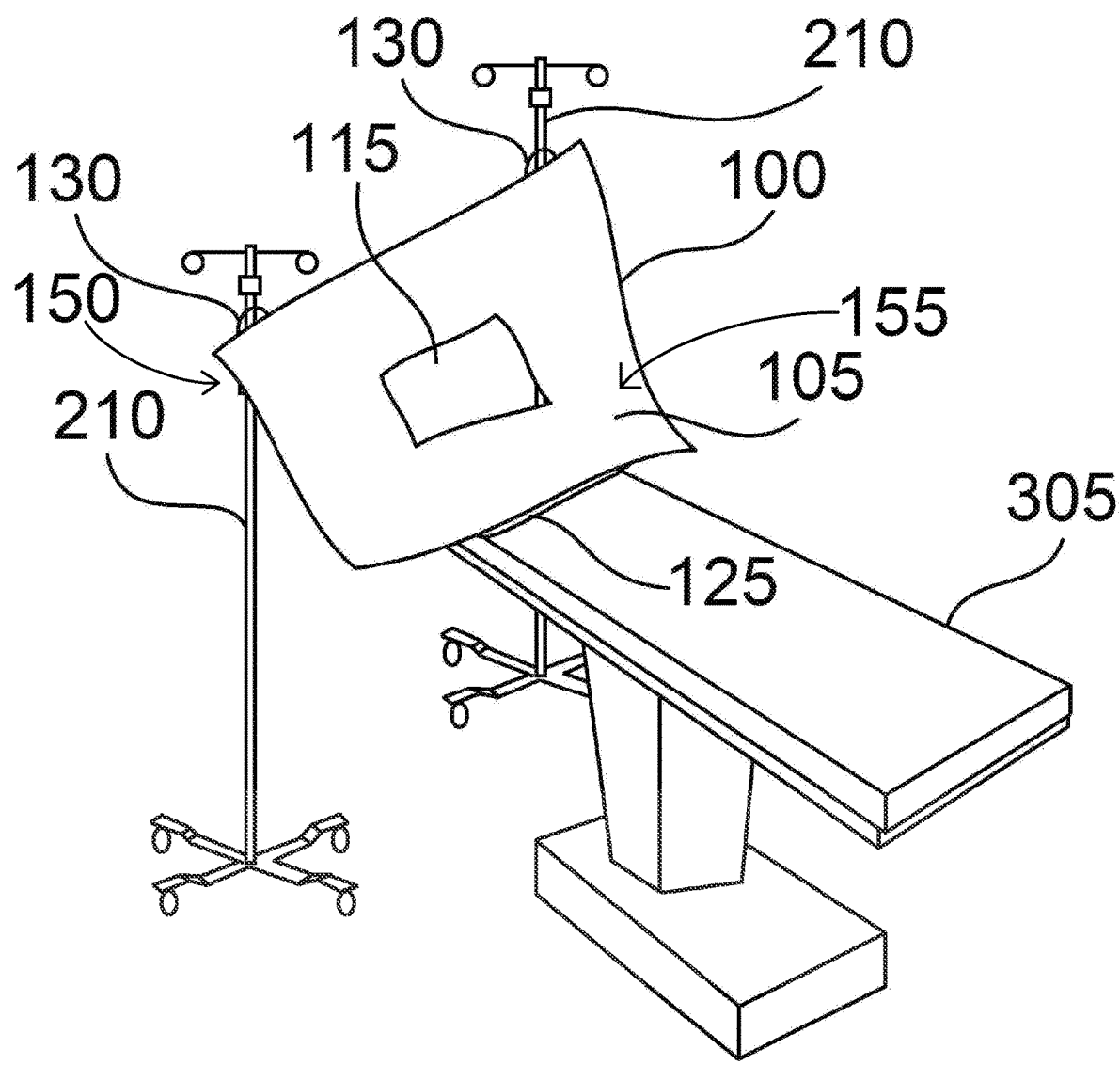
FIG. 3 is an example of a dedicated anesthesia surgical drape positioned over a surgical table, in accordance with various embodiments of the present disclosure.

According to various embodiments, the surgical drape 100 includes a front surface 105 and a back surface 110, the front surface 105 and the back surface 110 having a width sufficient to cover a surface of a surgical bed 305 (as shown in FIG. 3). As herein described, "surgical bed" 305 may include an operating table, a medical examination table, a hospital bed, and/or any other surface configured to enable a medical professional to perform one or more medical procedures.

According to various embodiments, the surgical drape 100 includes a transparent or partially transparent window section 115 configured to enable one or more medical professionals to see through the surgical drape 100. In order to prevent viewing through the window section 115, the surgical drape 100 may include one or more window covers 140 configured to be placed over the window section 115, blocking or partially blocking the view through the window section 115. The one or more window covers 140 may be permanently secured to the surgical drape 100 at one or more points on the surgical drape and/or may be entirely removable form the surgical drape 100. The drape 100 may include one or more fastening mechanisms 145 for securing the window section 115 in an upward position (enabling viewing through the window section 115) and/or in a downward position (blocking the view through the window section 115). The one or more fastening mechanisms 145 may include, for example, one or more adhesives, magnets, clips, buttons, snap fasteners, hook and loop fasteners, and/or any other suitable form of fastening mechanism.

Additionally and/or alternatively, the surgical drape 100 may include one or more pocket sections 120. The one or more pocket sections 120 may be positioned on one or more surfaces of the surgical drape 100. For example, as shown in FIG. 2, the one or more pocket sections 120 may be positioned on the back surface 110 of the surgical drape 100.

The surgical drape 100 may be configured to be coupled to a portion of a surgical bed 305 and/or to the patient via one or more surgical coupling mechanisms 125. The surgical coupling mechanisms 125 may include, for example, one or more adhesives, magnets, clips, buttons, snap fasteners, hook and loop fasteners, and/or any other suitable form of coupling mechanism(s) configured to maintain a sterile barrier between the anesthesia administration area 150 and the surgical area 155. The surgical coupling mechanism 125 may include one or more antimicrobial and/or antibacterial adhesives configured to maintain sterility of the surgical area 155. The antimicrobial and/or antibacterial adhesives may include one or more antimicrobial and/or antibacterial materials and/or compounds. The surgical coupling mechanism 125 may be positioned on a lower portion of the surgical drape 100, as is shown in FIG. 1. However, it is noted that the surgical coupling mechanism 125 may be located at any suitable position of the surgical drape 100.

According to various embodiments, the surgical drape 100 includes one or more upper coupling mechanisms 130 configured to secure the surgical drape 100 to one or more upper retention devices such as, for example, one or more intravenous (IV) poles or stands and positioned against an upper portion of the back surface 110 of the surgical drape 100. The one or more upper coupling mechanisms 130 are configured to enable the surgical drape 100 to be permanently or removably coupled to one or more IV poles 310 (as shown in FIG. 3). The one or more upper coupling mechanisms 130 may include an adhesive (e.g., glue), hook and loop fasteners, buttons, clips, magnets, and/or any other suitable form of coupling mechanism(s). According to various embodiments, the one or more upper coupling mechanisms 130 each include a plurality or arm portions 135 configured to wrap around a portion of the IV pole 310.

According to various embodiments, the front surface 105 is sterilized. After securing the surgical drape 100 against the surgical bed 305 using the one or more surgical coupling mechanisms 125, and securing the surgical drape 100 to the one or more IV poles 310 using the one or more upper coupling mechanisms 130, the surgical drape forms a barrier separating the anesthesia administration area 150 (located adjacent to the back surface 110 of the surgical drape 100) from any remaining surgical areas 155 which are open to the front or sterile surface 105 of the surgical drape 100. According to various embodiments, the sterile surface is sterilized prior to use.

The surgical drape 100 includes one or more materials configured to prevent nonsterile surfaces and materials from coming into contact with sterile surfaces and materials. These materials may include durable and flexible materials such as, for example, textiles which are tightly-woven (e.g., cotton, polyester, etc.), non-woven textiles (e.g., synthetic materials such as plastic), and/or any other suitable materials configured to maintain sterility of the surgical area 155. Due to the increased risk of pathogen spread when materials become wet, the front surface 105 and/or the back surface 110 of the surgical drape 100 may include one or more materials configured to resist the transmission of liquids through the surgical drape 100.

Referring to FIG. 3, a dedicated anesthesia surgical drape 100 positioned over a surgical bed 305 is illustratively depicted in accordance with various embodiments of the present disclosure.

As shown in FIG. 3, the surgical drape 100 may be positioned over a patient on a surgical bed 305 with the surgical coupling mechanism 125 facing the surgical bed 305 and, vicariously, the patient. The upper portion of the surgical drape 100 is coupled to one or more IV poles 310 positioned behind or to the side of the surgical bed 305, forming a draped covering over a portion of the patient in the area 150 designated for the administration of anesthesia during one or more medical procedures. The surgical coupling mechanism 125 creates a sterile barrier between the surgical area 155 and the anesthesia administration area 150.

Figure 4:
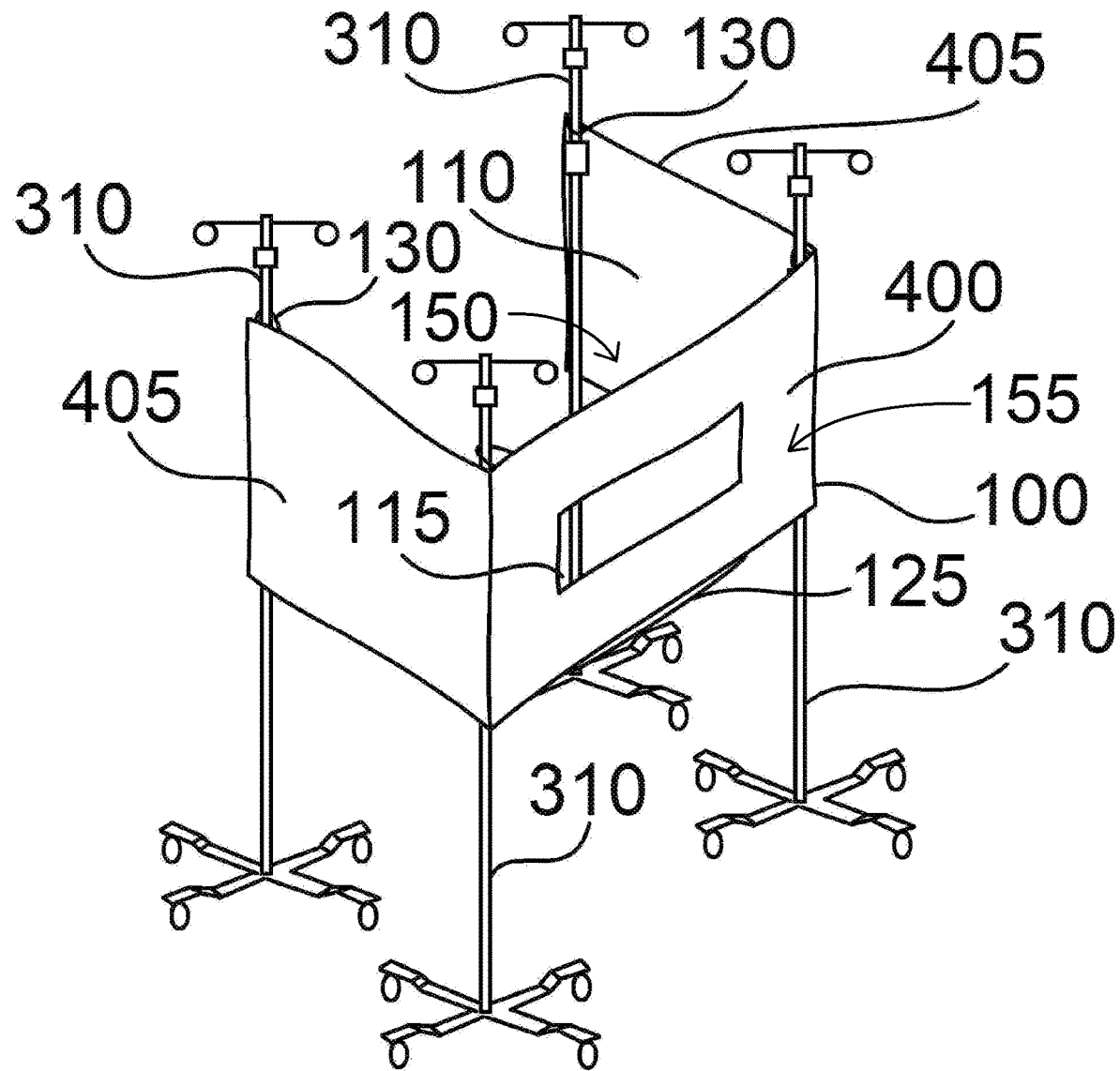
FIG. 4 is an example of a dedicated anesthesia surgical drape secured to a plurality of IV poles, in accordance with various embodiments of the present disclosure.

According to various embodiments, the surgical drape 100 may include a center portion 400 and one or more side portions 405, as shown in FIG. 4. The one or more side portions 405 are configured to further enclose the anesthesia administration area 150 from the surgical area 155. Each of the center portion 400 and the one or more side portions 405 includes a front surface 105 and a back surface 110. Each of the center portion 400 and the one or more side portions 405 may include one or more windows 115, one or more pocket portions 120, one or more surgical coupling mechanisms, and/or one or more upper coupling mechanisms 130.

As shown in FIGS. 1-4, the surgical drape 100 is rectangular in shape. It is noted, however, that the surgical drape 100 may take the form or any suitable shape or shapes such as, for example, rectangular, circular, rhomboid, oval, triangular, and/or any other suitable shape or shapes. The surgical drape 100 may be of any suitable thickness.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A surgical drape for separating an anesthesia administration area from a surgical area, comprising:
   a sterile front surface;
   a back surface;
   a surgical coupling mechanism configured to secure a lower portion of the surgical drape on a portion of a patient; and
   one or more upper coupling mechanisms configured to secure an upper portion of the surgical drape to one or more retention devices.

2. The surgical drape of claim 1, further comprising one or more window portions configured to enable a transparent view through the sterile front surface and the back surface.

3. The surgical drape of claim 2, further comprising one or more window coverings configured to cover one or more portions of the one or more window portions.

4. The surgical drape of claim 1, further comprising one or more pocket portions positioned on the sterile front surface or the back surface.

5. The surgical drape of claim 1, wherein the surgical coupling mechanism includes one or more of the following:
   one or more adhesives;
   one or more hook and loop fasteners; or
   one or more snap fasteners.

6. The surgical drape of claim 5, wherein the one or more adhesives includes one or more antimicrobial adhesives.

7. The surgical drape of claim 1, wherein the surgical coupling mechanism forms a sterile barrier.

8. The surgical drape of claim 1, wherein the sterile front surface includes one or more of the following:
   plastic;
   polyester; or
   cotton.

9. The surgical drape of claim 1, wherein the one or more upper coupling mechanisms includes one or more of the following:
   one or more adhesives;
   one or more hook and loop fasteners;
   one or more buttons;
   one or more clips; or
   one or more snap fasteners.

10. The surgical device of claim 1, wherein the one or more retention devices includes one or more intravenous poles.

11. A surgical drape for separating an anesthesia administration area from a surgical area, comprising:
    a center portion;
    one or more side portions,
        wherein the center portion and the one or more side portions each include a sterile front surface and a back surface;
    a surgical coupling mechanism configured to secure a lower portion of the surgical drape on a portion of a patient; and
    one or more upper coupling mechanisms configured to secure an upper portion of the surgical drape to one or more retention devices.

12. The surgical drape of claim 11, further comprising one or more window portions configured to enable a transparent view through the sterile front surface and the back surface.

13. The surgical drape of claim 12, further comprising one or more window coverings configured to cover one or more portions of the one or more window portions.

14. The surgical drape of claim 11, further comprising one or more pocket portions positioned on the sterile front surface or the back surface of the center portion or the one or more side portions.

15. The surgical drape of claim 11, wherein the surgical coupling mechanism includes one or more of the following:
   one or more adhesives;
   one or more hook and loop fasteners; or
   one or more snap fasteners.

16. The surgical drape of claim 15, wherein the one or more adhesives includes one or more antimicrobial adhesives.

17. The surgical drape of claim 11, wherein the surgical coupling mechanism forms a sterile barrier.

18. The surgical drape of claim 11, wherein the sterile front surface includes one or more of the following:
   plastic;
   polyester; or
   cotton.

19. The surgical drape of claim 11, wherein the one or more upper coupling mechanisms include one or more of the following:
   one or more adhesives;
   one or more hook and loop fasteners;
   one or more buttons;
   one or more clips; or
   one or more snap fasteners.

20. The surgical device of claim 11, wherein the one or more retention devices include one or more intravenous poles.

* * * * *